United States Patent
Brasile

(10) Patent No.: US 8,078,260 B2
(45) Date of Patent: Dec. 13, 2011

(54) METHOD FOR IMPROVING MAGNETIC RESONANCE IMAGING OF THE BREAST

(75) Inventor: Lauren Brasile, Albany, NY (US)

(73) Assignee: ORGAMEND Inc., Albany, NY (US)

( * ) Notice: Subject to any disclaimer, the term of this patent is extended or adjusted under 35 U.S.C. 154(b) by 0 days.

(21) Appl. No.: 11/945,207

(22) Filed: Nov. 26, 2007

(65) Prior Publication Data

US 2008/0214930 A1 Sep. 4, 2008

Related U.S. Application Data

(63) Continuation-in-part of application No. 11/743,467, filed on May 2, 2007, now abandoned.

(60) Provisional application No. 60/797,056, filed on May 2, 2006.

(51) Int. Cl.
*A61B 5/05* (2006.01)

(52) U.S. Cl. .................................. 600/422; 600/410

(58) Field of Classification Search .......... 600/407–422; 324/309, 318–322
See application file for complete search history.

(56) References Cited

U.S. PATENT DOCUMENTS

| | | | | |
|---|---|---|---|---|
| 5,339,033 A * | 8/1994 | Eilenberg et al. | ............. | 324/309 |
| 5,414,358 A * | 5/1995 | Eilenberg et al. | ............. | 324/309 |
| 6,850,065 B1 * | 2/2005 | Fujita et al. | ............. | 324/318 |
| 6,887,210 B2 * | 5/2005 | Quay | ............. | 600/573 |
| 7,034,530 B2 * | 4/2006 | Ahluwalia et al. | ............. | 324/309 |
| 7,084,631 B2 * | 8/2006 | Qu et al. | ............. | 324/318 |
| 7,128,877 B2 * | 10/2006 | Quay et al. | ............. | 600/573 |
| 7,386,338 B2 * | 6/2008 | Hoppel et al. | ............. | 600/422 |
| 7,514,926 B2 * | 4/2009 | Adriany et al. | ............. | 324/318 |
| D622,389 S * | 8/2010 | Henke-Sarmento | ............. | D24/158 |
| 2001/0007076 A1 * | 7/2001 | Jesseph | ............. | 606/130 |
| 2005/0104591 A1 * | 5/2005 | Qu et al. | ............. | 324/318 |
| 2005/0245805 A1 * | 11/2005 | Hoppel et al. | ............. | 600/407 |
| 2006/0270930 A1 * | 11/2006 | Brasile | ............. | 600/410 |
| 2007/0092059 A1 * | 4/2007 | Wayne Eberhard et al. | ............. | 378/37 |
| 2008/0103387 A1 * | 5/2008 | Gross | ............. | 600/424 |
| 2008/0177180 A1 * | 7/2008 | Azhari et al. | ............. | 600/439 |
| 2010/0041979 A1 * | 2/2010 | Harter | ............. | 600/411 |

* cited by examiner

*Primary Examiner* — Sanjay Cattungal
(74) *Attorney, Agent, or Firm* — Heslin Rothenberg Farley & Mesiti P.C.; Kathy Smith Dias, Esq.

(57) ABSTRACT

The present invention provides a fat saturation device to be used in conjunction with a magnetice resonance imaging (MRI) breast coil, which provides padding for the comfort of the patient being imaged while eliminating the skin-air interface, thereby reducing the level of artefacts in the image. The device comprises a coil surface pad that contacts the surface of the coil, the pad having apertures therein through which the patients breasts extend when the patient is positioned on the coil for imaging. Aperture sleeves that are removable or retractable extend from the bottom surface of the coil surface into the apertures of the breast coil. The device comprises a fat saturation material.

10 Claims, 8 Drawing Sheets

METHOD FOR IMPROVING MAGNETIC RESONANCE IMAGING OF THE BREAST

CROSS REFERENCE TO RELATED APPLICATIONS

This application is a continuation-in-part of U.S. application Ser. No. 11/743,467, filed May 2, 2007, now abandoned, which claims the priority of U.S. provisional application Ser. No. 60/797,056, filed May 2, 2006, the contents of which are hereby incorporated by reference into the present application.

FIELD OF THE INVENTION

The invention relates to a device and method for improving magnetic resonance imaging of the breast. More particularly, the invention relates to enhanced breast imaging by filling the void area between the breast coil aperture and breast tissue with a self-contained pad that conforms specifically to the three-dimensional surfaces of the breast coil while simultaneously accommodating differences in breast anatomy.

BACKGROUND OF THE INVENTION

Magnetic resonance imaging (MRI) of the breast has emerged as an important new diagnostic tool for the detection of tumors. Pre-surgical MRI can help to reduce the number of biopsies that need to be taken by distinguishing benign from malignant tumors. Likewise, MRI techniques provide opportunities for staging malignant tumors that can play an important role in breast preserving surgery. More recently MRI has been employed to achieve MR-guided subcutaneous core biopsies, allowing for coordination of minimally invasive surgery. Introducing contrast agents such as gadolinium-diethylene triamine-pentaacetic acid (Gd-DTPA) during MR imaging provides sensitivity approaching 100%. An added benefit of MRI is the ability to accomplish sentinel node identification with simultaneous fat suppression. Following surgery for tumor excision, MRI is the modality of choice for the detection of residual disease. MRI is also the modality of choice for evaluating the integrity of breast implants.

The components involved in magnetic resonance imaging (MRI) include a primary magnet, computer controlled shim coils to produce field homogeneity, gradient coils to generate linear fields, radio frequencies (rf) for transmitting rf pulses and also for receiving MR imaging signals unless separate receiving coils are integrated and advanced specialized software for data acquisition, analysis and pulse sequence. MR imaging involves exposing nuclei to a strong magnetic field and then excitation by rf resonant energy.

Despite the sensitivity MR imaging provides over more traditional imaging modalities such as mammography or ultrasound, there are several technologic hurdles. While providing exceptional sensitivity, it displays variable specificity that represents a major limitation. An area of concern given the varying specificity is the patient management decisions when tumors are detected by MR imaging that can not be identified with more traditional imaging modalities.

To aid enhanced MR imaging of the breast, MRI equipment manufacturers have developed and marketed breast coils. Breast coils are usually whole-volume solenoids used for transmission and receiving. Resonators are applied over the breast, usually in pairs to allow for simultaneous imaging of both breasts. The quality of the MR image produced can be enhanced by the optimal use of an independent coil placed close to the area being imaged in order to improve the strength of any received signal and are called surface coils. Many of the breast coils are system/manufacturer specific. While the aperture configuration and dimensions of the various breast coils may vary slightly, all breast coils presently in commercial use, receive (position) the breasts of women while lying face down and can image both unilaterally and bilaterally. RF coils designed specifically for imaging breast tissue are described in more detail, for example, in U.S. Pat. Nos. 6,850,065, 6,198,962, 6,163,717, and 5,706,812.

For example, a breast coil designed by MRI Devices Corporation and marketed by General Electric uses an open design with a sternum pad that provides lateral access to either breast for patient positioning. The General Electric employs dual apertures for imaging breasts with a rectangular configuration of approximately 4.75 inches by 7.25 inches to position the breasts of women. Not being limited by the view provided by a lateral window, the hanging breasts can be viewed from all angles.

Similarly, Toshiba Medical Systems markets a breast array coil that can be used to image the female breast, chest wall and axillae. Toshiba's breast coil uses a four-channel phased array in the receive mode exclusively. A side window in the breast coil allows visualization of the exposed breasts by the MRI technician to ensure proper placement of the breasts within the breast coil.

The Siemens Medical Systems breast array coil also lies directly on the table within the magnetic field. Similarly, the design also allows for visual control of the position of the breasts within the breast coil through a transparent window on the side of the coil that is performed by the MRI technician. The four-coil design with four independent preamplifiers employ stability pads that are located on the sides of the coil apertures that are used to compress the breast tissue and to adjust for wide variation in anatomical dimensions.

The breast coil of Hitachi Medical Systems is similar in design to both those of Toshiba and Siemens. It is a quatrature coil for bilateral breast, chest wall and auxiliary node imaging. Similar to the other commercially available breast coils, the woman lies face down with pendulantly suspended breasts positioned in the two coil apertures and compressed to accommodate for varying breast size by the technician using visual access.

Philips uses a 4-channel phased array breast coil for both unilateral and bilateral imaging of the breast, chest wall and axillary tissue. The 4-channel array design uses open architecture that allows for interventional access with easy biopsy and needle placement. The Philips coil uses oval apertures of 16 cm diameter and 12 cm depth to accommodate the variations in breast size.

In using all of the above mentioned breast coils, the woman lies prone face down and head first. The breasts must be positioned in the center of the coils. Since there is a tendency for patients to slide too far superiorly in the coil, they are usually asked to slide towards their feet after lying prone on the coil support. The various breast coils used clinically are all made of hard molded plastics. Since the breasts are suspended pendulantly, below the surface of the breast coil, the weight of the patient is placed on the chest bones. To make the procedure more comfortable a high resilience, high density foam pad with the same diameter and aperture configuration of the coil is placed on the top surface of the coil. The patient lies on top of the coil pad. However, the coil pads are 2-dimensional and do not provide image enhancement by either fat saturation or by reducing the skin to air interface.

The salient feature common to all of these breast coils is the need to adequately position women's breasts that are hanging pendulantly. Another common feature of the breast coils in proper positioning breasts within the coil is the aspect of using some form of compression to immobilize the breasts and adapt the apertures for variation in individual breast size. These "one size fits all" breast coils rely on filling the residual volume between the breast tissue aperture space manually by the MR imaging technician that is visibly guided and manual (FIG. 1). This residual space is filled using materials placed within the coil aperture such as dielectric pads or by compression with plastic spacers.

The non-uniformities in the magnetic resonance system's main magnetic field that is generated by the variations in breast geometry and magnetic susceptibility in localized areas of the breast can be problematic in obtaining good quality images. Fat suppression is an imaging technique that relies on changing the relative brightness of fat in comparison to water in order to obtain a better quality image. However, the fat saturation techniques used in magnetic resonance imaging are highly sensitive to homogeneity in the magnetic field and breast anatomy is not homogenous in areas. Specific areas of concern are the areas where the breast and chest wall interface. The techniques attempt to selectively excite fat with a narrow band RF pulse that has the characteristic resonance frequency of fat, while leaving water unaffected. Fat saturation techniques while beneficial, may not uniformly suppress the fat within the breast tissue being imaged and can result in cross-suppression where water molecules may be likewise affected. The result is unreliable fat saturation with a less than optimal image.

Another method for controlling the homogeneity of the magnetic field includes both passive and active shimming techniques. The passive techniques is typified by arranging steel shims to minimize static magnetic field inhomogeneities at diameters comparable to the gradient coils. A major shortcoming of passive shimming is not adjustable from scan to scan.

Active shimming uses shim coils that can be adjusted to establish uniform magnetic fields by integrating the localized shim coil into a RF coil. The localized shim coil can then be engaged during a fat saturation pulse sequence that is being transmitted by the magnetic resonance system. While contributing to image enhancement, shimming may not uniformly suppress fat and can suppress regions of water in the breast.

Another method to enhance fat saturation during magnetic resonance imaging of the breast is the use of a flexible bag containing a variable amount of a fat saturation enhancing material that surrounds a flexible coil. U.S. Pat. No. 5,414,358 describes a bag made preferably of polyurethane and filled with a perfluorochemical liquid. The breast bag is connected to an inlet pipe which has a pump and an outlet pipe having a shut-off valve. A reservoir is connected to the opposite ends of both the inlet and the outlet pipes. When the bag is emptied of the perfluorochemical liquid a hollow center forms into which breast can be inserted. The bag is then refilled by opening the inlet valve, then turning on the pump to feed the perfluorochemical liquid into the inlet pipe from the reservoir and at the same time closing the valve in the outlet pipe. The flexible bag is secured to the coil and the patient by means of straps. There are several significant drawbacks to this device. First, it is not compatible for use with any of the breast coils being used clinically. The breasts placed in the breast bag cannot be further placed into the breast coil apertures since the base of the breast bag is contiguous and flat. Secondly, the volume of fat saturation enhancing material that is re-introduced is variable without intrinsic controls to ensure there is enough material present to provide adequate image enhancement. Thirdly, the breasts are compressed by the weight of the patient laying prone on the breast bag and subsequently further compressed when the bag is refilled with the perfluorochemical liquid after being inflated. Hence, the breasts are compressed from two sides by the weight of the woman and by the simultaneous pressure of the perfluorochemical in the inflated breast bag. The resulting compression of the breast tissue negatively impacts the ability to image the vasculature and lesion angiogenesis. Fourthly, the selectively fillable breast bags covers the breasts on all sides making biopsy impossible. The opportunity to perform the biopsies that are an integrated component of the breast coils is eliminated.

U.S. Pat. Nos. 5,414,358 and 5,339,033 issued to Eilenberg et al. describe a method for improving fat saturation during MRI. The method uses a pad containing a fat saturation material, where the pad is applied to the anatomy to be imaged.

Interventional MRI procedures typically require that an MR signal detection coil have large openings so that a surgeon can have access to the surgical site through the coil with a biopsy needle or other surgical devices. However, in the absence of a fat saturation device, artifacts are common. The difficulty in providing surgical access is especially difficult for breasts, due to the varying sizes and shapes and desirability of minimizing manipulation which is stressful for the patient. What is needed is a fat saturation device specifically designed for use in conjunction with breast coils.

SUMMARY OF THE INVENTION

The present invention provides a method for enhancing the magnetic resonance (MR) image of breast tissue by employing a device comprising a fat saturation material wherein the device is designed to be used in conjunction with a radio frequency (rf) coil for magnetic resonance imaging of the breasts. For example, a self-contained, 3-dimensional pad that is positioned on the surface of the MR imaging breast coil, replaces the need for conventional high resilience, high density pads. The device of the invention also lines the coil apertures receiving the patient's breasts, thereby partially enclosing the coil. The 3-dimensional MR imaging pad can be positioned on the breast coil prior to use and requires no further manipulations. The 3-dimensional breast pad interfaces closely with any breast coil and can effectively reduce the skin to air interface regardless of breast size.

In one aspect, therefore, the invention relates to a device for enhancing magnetic resonance imaging of a breast comprising a first contoured surface comprising a pair of apertures for receiving the breast wherein said apertures are surrounded by a flexible sleeve that conforms snugly to a portion of the breast near the chest wall and wherein said device comprises a fat saturation material.

In a related aspect, the invention relates to a device for enhancing magnetic resonance imaging of a breast comprising a plurality of releasably attachable pad components comprising a fat saturation material wherein said components are attached to each other in a configuration so as to define a pad comprising a pair of apertures for receiving the breasts to be imaged wherein the breasts are encircled by a flexible sleeve that conforms snugly to a portion of the breast near the chest wall. The device is adapted to be positioned between the chest wall of the patient and the imaging coil with the breasts extending through the device.

In a related aspect, the invention relates to a method of improving magnetic resonance imaging of the breast, the method comprising the steps of providing a device comprising a first contoured surface comprising a pair of apertures for receiving the breast wherein said apertures are surrounded by a flexible sleeve that conforms snugly to a portion of the breast near the chest wall and wherein said device comprises a fat saturation material and wherein said device is positioned on the rf coil prior to imaging; and imaging said breast with a magnetic resonance imaging system.

DETAILED DESCRIPTION OF THE INVENTION

Figure 1:
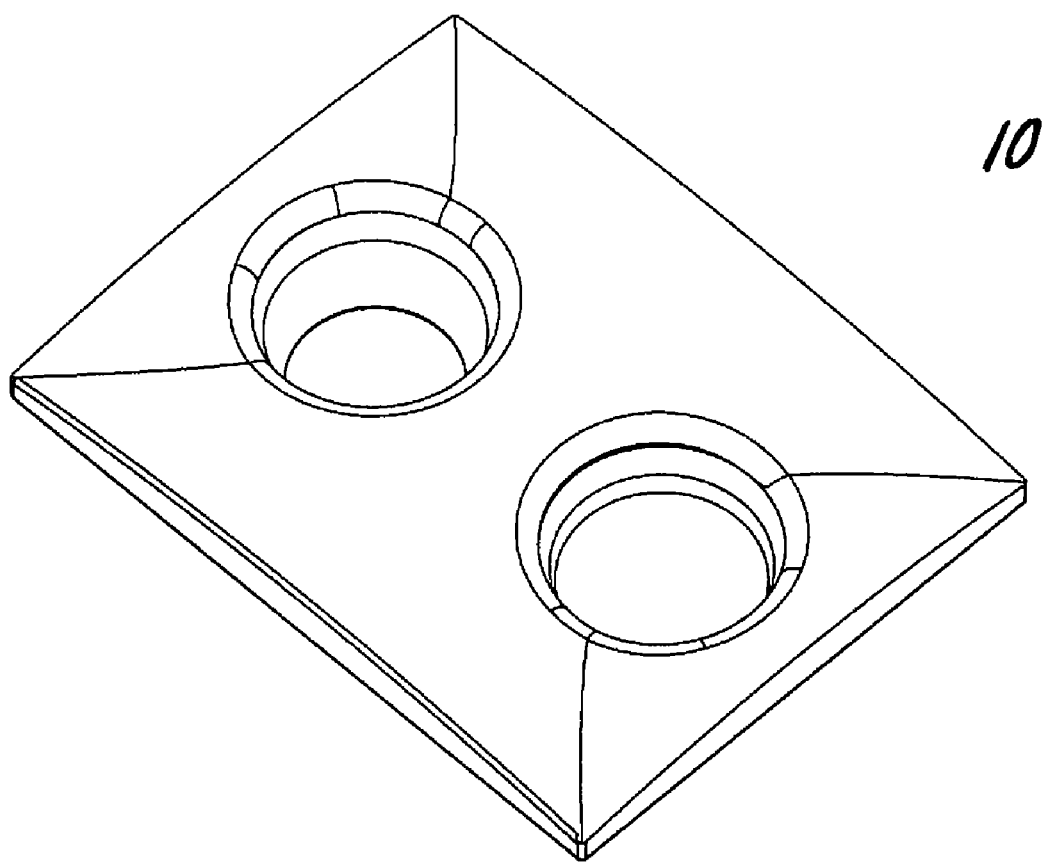
FIG. 1 is a perspective view of the top of an embodiment of the device of the invention.
Figure 2:
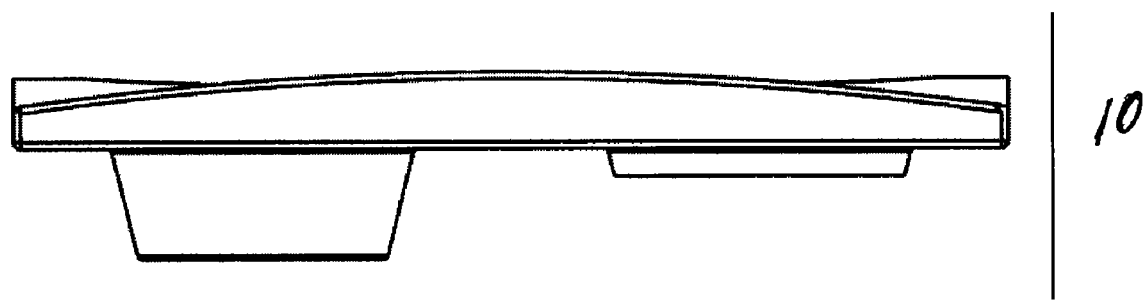
FIG. 2 is a side view of the embodiment shown in FIG. 1.
Figure 3:
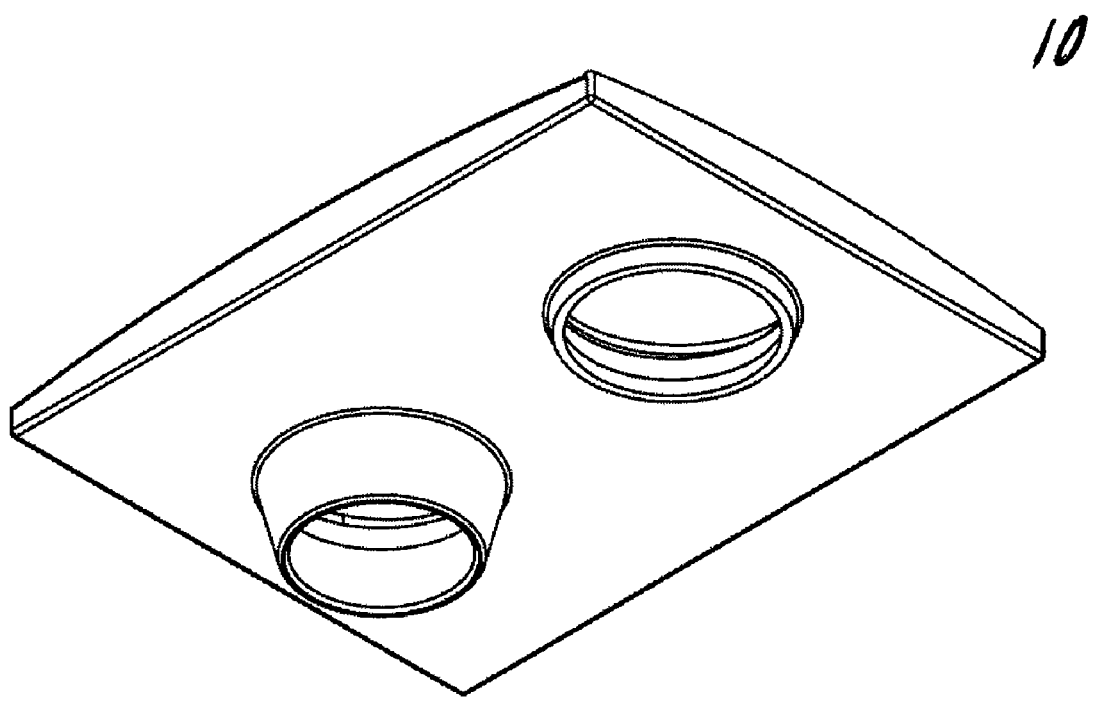
FIG. 3 is a perspective view of the bottom of an embodiment of the device of the invention.

All patents, published applications, and other references cited herein are incorporated by reference in the present disclosure.

The present invention provides a method and device that specifically enhances fat saturation for magnetic resonance imaging of breast tissue. The object of the device is to fill the void space surrounding the tissue to be imaged. Accordingly, the device is designed to occupy the space between the breasts, as well as space between the breasts and the coil without compressing the breast vasculature or interfering with interventional procedures.

In one embodiment, the device of the present invention is constructed of releasably attachable or removable components and can be configured to fit a variety of rf coils, including but not limited to those described in U.S. Pat. Nos. 6,850,065, 6,198,962, 6,163,717, and 5,706,812 for example. Furthermore, the component parts, which cover the lower portion of the coil can be removed or retracted to permit intervention, for example, needle biopsy, concurrently with imaging. Additionally, the fat saturation enhancing device of the invention functions as a cushioning pad that covers the surface of the breast coils that patients lie upon.

The fat saturation enhancing system is designed with a three-dimensional structure that covers the surface of the coil (coil-contacting surface) and additionally, partially encloses the open space of the coil thereby filling the space between the coil to be used in imaging the breast and the breast tissue itself. The fat saturation enhancing system contains an appropriate amount of fat saturating material to yield a self contained pad that is flexible enough to conform to the shape of the patient being imaged, and is able to maintain contact with the rf coil. The pad is positioned so that its bottom surface is in contact with the surface of the coil and the upper surface of the pad is in contact with the patient with vertical components of the pad suspended downward to fill the sides of the coil aperture, leaving the bottom area open. There is no need to selectively adjust the volume of the three-dimensional pad to accommodate variations in breast size. Rather, the open bottom area of the fat saturation pad is flexible allowing for the device to move either convexly (outwardly) around the bottom of the coil to accommodate larger breasts; or concavely (inwardly) to accommodate smaller breasts while reducing the skin to air interface. The open bottoms of the fat saturation enhancing pad in tandem with the corresponding flexibility on the bottom edges allows for biopsy procedures that are inherent to coil designs used clinically. The fat saturation enhancing device supports the breast on a perpendicular plane to the spine while simultaneously providing an aperture to involve the whole breast and auxiliary node areas. The fat saturation enhancing device is designed to avoid breast compression that would negatively impact imaging of the vasculature and identification of lesion angiogenesis.

Figure 4:
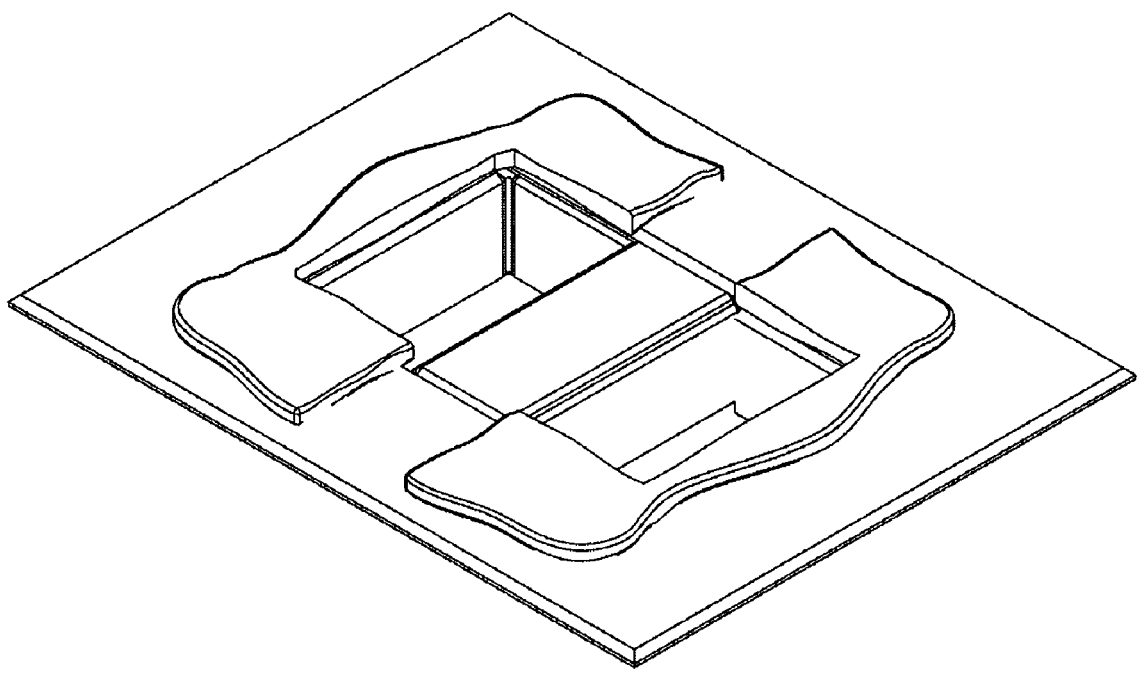
FIG. 4 is a perspective view of the top of one embodiment of the invention having rectangular apertures.
Figure 5:
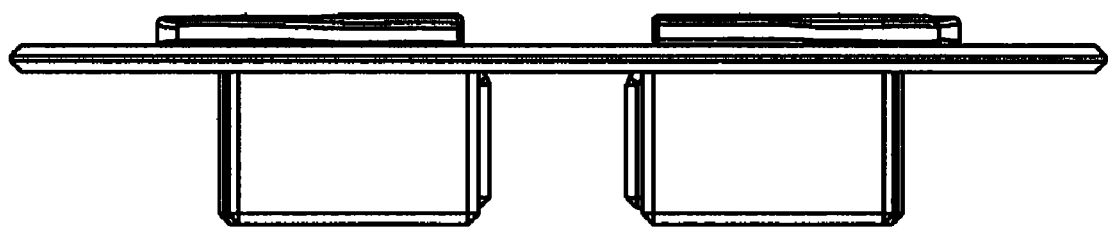
FIG. 5 is a side view of the embodiment shown in FIG. 4.
Figure 6:
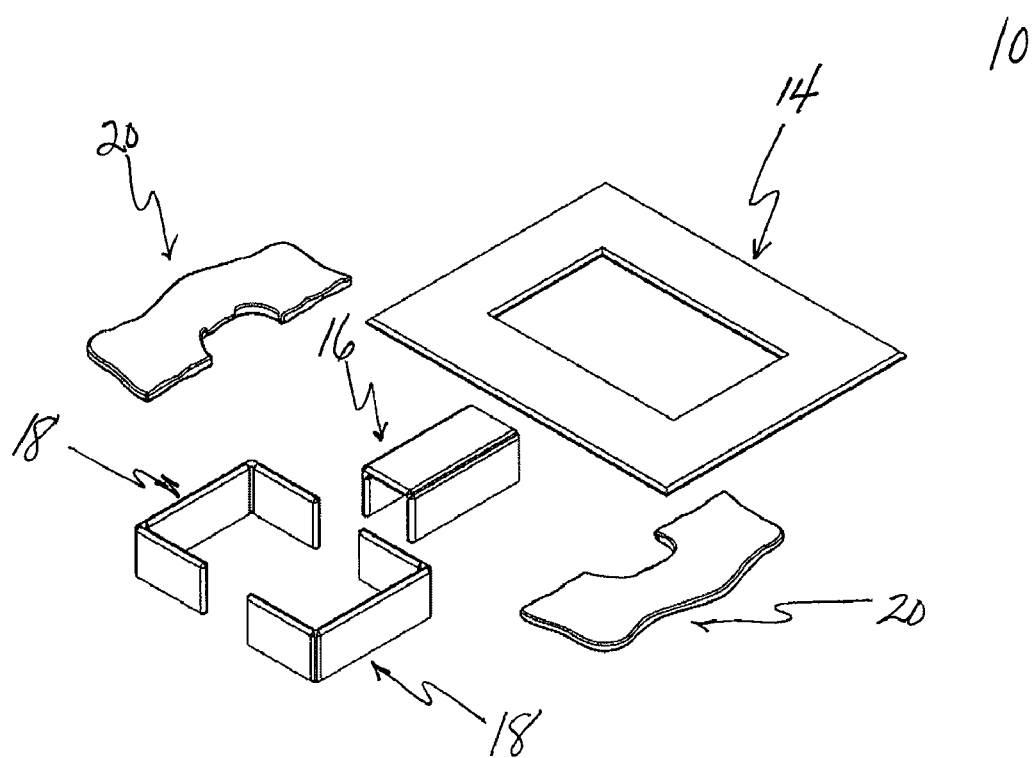
FIG. 6 is an exploded view of the embodiment of the invention shown in FIG. 4.

In one embodiment, as shown in FIGS. 4-6, the fat saturation device of the invention (10) comprises a plurality of releasably attachable components: a coil surface pad (14), an aperture separator pad (16) and aperture sleeves (18) and optionally, additional padding strips (20) which are positioned on top of the assembled device (10) and provide extra padding to the surface of the device which contacts the woman's chest. The overall contour of the various components may vary, for example, the aperture separator pad and aperture sleeves may be more rounded than rectangular.

The aperture sleeve (18) surrounding the surface coil can be detached from the coil surface pad (14) on the top of the breast coil to gain access to the breast for the purpose of performing a biopsy to the degree allowed by the design of the coil configuration. Alternatively, the aperture sleeve of some embodiments can be retracted for the purpose of performing interventional procedures.

The design of the fat saturation device for magnetic resonance imaging of the breast eliminates the need to secure the device to the patient. Likewise, since the device fits snuggly on top and within the breast coil there is also no need to employ strapping or other attaching methods to provide close and stable contact with the breast coil.

In another embodiment, the fat saturation device of the present invention is molded from a fat saturation material, such as Teflon® to form a single unit having a contoured surface and apertures therein; the interior perimeter of the aperature(s) communicates with an aperture sleeve that extends downward. In this embodiment, aperture sleeves may be releasably attached or an integral part of the unit and retractable, for example, by rolling or folding the sleeve upward on itself.

The fat saturation device can be applied to a breast coil by the radiology technician prior to the patient's arrival. No further adjustments are necessary before or while a patient is being positioned for magnetic resonance imaging. The elimination of time consuming manipulations is important in MR imaging centers where time correlates with cost. Unlike the device described in U.S. Pat. No. 5,414,358 (where the breast bag must be emptied, the breasts positioned, an inlet valve opened, outlet valve closed, the fat saturating material pumped into the bag and the whole procedure reversed), the fat saturation enhancing pad of the present invention once positioned on the coil requires no burdensome manipulations. Furthermore, access to the breast for biopsy is readily accomplished by removal or retraction of the sleeve encircling the breast.

Since the breasts to be imaged are positioned pendulantly in the magnetic resonance system, the fat saturation pad of the invention moves within the coil aperture and adjusts easily to accommodate variations in breast size; without intervention by the technician. The automatic adjustment of fat saturation enhancing pad is also beneficial in terms of efficiency since there is no need to alter the pad or reposition the patient, breasts or the device. In cases where a suspect lesion in the breast is proximal to the chest wall, the circumferential pad can be easily mobilized to expose the area to be biopsied.

EXAMPLE 1

In another configuration, the fat saturation enhancing pad can be constructed to provide two detachable pieces: the pad lining the top of the breast coil that the patient lays upon and the circumferential pad that covers the area surrounding the surface coil that surrounds the pendulant breast. By detaching the circumferential part of the device from the pad layering the top of the breast coil access to the breast can be achieved for the purpose of performing a biopsy.

EXAMPLE 2

In one embodiment, the fat saturation enhancing device can be fabricated to be used in combination with any of the various breast coils that are used clinically. In an industry where MR coils are manufacturer and system specific, the device can be configured to provide both three-dimensional circular and rectangular apertures to fit into the existing apertures in the various breast coils in use clinically.

EXAMPLE 3

In one embodiment, the device enhances fat saturation without compression of the breast tissue resulting in better imaging of the vasculature with enhanced identification of lesion angiogenesis. Moreover, the absence of breast tissue compression makes the device compatible with breast imaging software because its use does not alter the pendulant configuration of the breast when a patient lays prone on a breast coil.

EXAMPLE 4

In another embodiment, the device can be terminally filled with material(s) that enhance the image quality. Materials that provide added reinforcement and tensile strength will result in additional support, shape configuration and immobilization. In addition, an additional benefit of adding filling to the pad is the increased enhancement in image quality by superior fat saturation. Additional benefit eliminates the need for variable filling-factor and result in increased the signal-to-noise ratio. Lining the structural components of the device with materials such as perfluorochemicals, oils or non-protonated Teflon beads or particles, increases reception efficiency in effect increasing the RF sensitivity in collection of the signals and impacts the refractive index leading to improved signal quality. Improvements in signal quality in turn increase the signal-to-noise ratio resulting in better quality signals that provide better images.

EXAMPLE 5

In another embodiment, the fat saturation enhancing device can consist of an injection molded or thermoformed three-dimensional pad that completely fills the space between the patients breast and the breast coil. Similar to the other examples listed above, the injection molded or thermoformed device can accommodate variations in breast size by using plastics in combination with silicones to provide a high degree of flexibility. Similar to a pre-filled pad, the exterior of the device maintains a constant configuration in order to uniformly and completely fill the aperture of the breast coil around the breast. The molded device can be made to be semi-rigid, flexible or semi-flexible to varying degrees by employing teflons, silicones, plastic alloys made from various components and in various concentrations including commodity materials such as acrylics, PVCs, acrylonitrites, butadienes, styrenes, etc. Likewise, the molded components can be made from higher-end specialized materials with healthcare ratings, such as amorphous thermoplastic polyetherimide (PEI) resins, for example, Ultem™, siloxane-polyetherimide such as Siltem™ and modified polyphenylene oxides (PPO) such as Noryl™.

EXAMPLE 6

In another embodiment the fat saturation enhancing pad can utilize an injection molded outer piece used in conjunction with a similarly molded inner piece and filled with an imaging enhancing fluid to improve the quality of the image obtained with magnetic resonance. The improvements of combining a two-layered injection molded pad with an image enhancing fluid interface would be the elimination of pooling of the liquid and the risk of leakage due to puncture or rupture that occurs when using a film based pad.

Breast Pad Fieldmapping Overview
Datasets Analyzed
Fieldmap Scans:

Modulus and phase images were acquired with and without the use of the breast pad (BP). All the analyzed data were acquired without shimming procedure. Slice thickness 12 mm.

Figure 7:
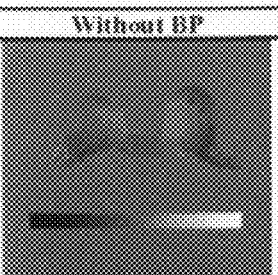
FIG. 7 depicts an aperture sleeve of one embodiment of the device of the invention.
Figure 8:
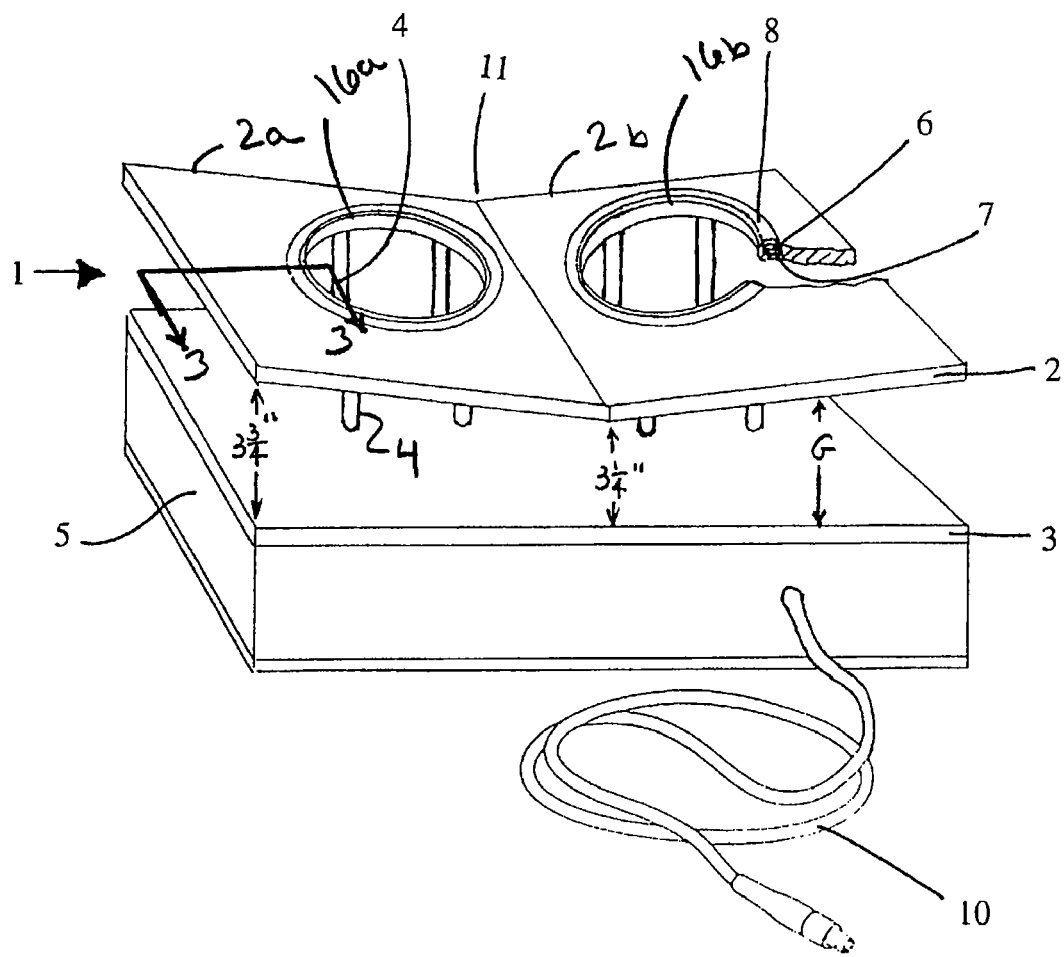
FIG. 8 is a schematic of an open structure breast coil and support arrangement used in interventional resonance imaging of the breast.

Data Post-Processing Steps:

Phase images were unwrapped and segmented. A $-2\delta$ to $2\delta$ scale was added. Per study, two slices phasemaps (without and with BP) are shown in FIG. 7. The use of the breast coil pad provided images with smaller variations in the intensity range. The smaller variances seen in FIG. 7 suggests a more homogeneous field was accomplished with use of the breast coil pad of the invention. All variances are taken from the full 3D, segmented dataset.

The invention claimed is:

1. A device for enhancing magnetic resonance imaging of a breast, said device comprising:
   a pad adapted for use in conjunction with a magnetic resonance imaging breast coil, said pad comprising a pair of apertures therethrough for receiving the breast and a flexible sleeve that extends downwardly from said pad, said sleeve being disposed in each of said apertures of the pad so that said sleeve extends into corresponding apertures of said magnetic resonance imaging breast coil, wherein said flexible sleeve is continuous with the pad so that the intersection of the pad and sleeve conforms snuggly to a portion of the breast near the chest wall and wherein said pad and sleeve comprise a fat saturation material.

2. The device of claim 1, wherein said device comprises:
   a plurality of releasably attachable components comprising a fat saturation material wherein when said components are attached to each other, said components define a pad comprising a pair of apertures for receiving the breasts to be imaged and a flexible sleeve that extends outwardly from said pad wherein a flexible sleeve is disposed in each of said apertures so that said sleeves are continuous with the pad so that the intersection of the pad and sleeve conforms snuggly to a portion of the breast near the chest wall.

3. The device of claim 1, wherein said sleeve is movable.
4. The device of claim 1, wherein said sleeve is removable.
5. The device of claim 1, wherein said sleeve is retractable.
6. The device of claim 1, wherein said sleeve is generally round in shape.

7. The device of claim 1, wherein said sleeve is generally rectangular in shape.

8. The device of claim 1 wherein said fat saturation material is non-protonated.

9. The device of claim 1 wherein said fat saturation material is selected from the group consisting of perfluorochemicals, TEFLON®, amorphous thermoplastic polyetherimide resins, siloxane-polyetherimide, modified polyphenylene oxides and combinations thereof.

10. The device of claim 1 wherein said fat saturation enhancing material is selected from the group consisting of perfluorooctylbromide (PFOB), perfluorodecylbromide (PFDB), FC-77 and FC-43.

* * * * *